(12) United States Patent
Wang et al.

(10) Patent No.: US 8,968,354 B2
(45) Date of Patent: Mar. 3, 2015

(54) EXTENDED PROTECTION EMBOLIC FILTER

(71) Applicant: Boston Scientific Scimed, Inc., Maple Grove, MN (US)

(72) Inventors: Huisun Wang, Maple Grove, MN (US); James M. Anderson, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 79 days.

(21) Appl. No.: 13/659,051

(22) Filed: Oct. 24, 2012

(65) Prior Publication Data

US 2013/0110153 A1    May 2, 2013

Related U.S. Application Data

(60) Provisional application No. 61/551,633, filed on Oct. 26, 2011.

(51) Int. Cl.
*A61M 29/00* (2006.01)
*A61F 2/01* (2006.01)
*A61F 2/95* (2013.01)

(52) U.S. Cl.
CPC . *A61F 2/013* (2013.01); *A61F 2/01* (2013.01); *A61F 2002/011* (2013.01); *A61F 2002/016* (2013.01); *A61F 2002/018* (2013.01); *A61F 2002/9511* (2013.01); *A61F 2002/9528* (2013.01); *A61F 2230/0095* (2013.01); *A61F 2230/0008* (2013.01); *A61F 2230/0069* (2013.01); *A61F 2230/0076* (2013.01); *A61F 2230/008* (2013.01)
USPC ......................................... 606/200

(58) Field of Classification Search
CPC ................ A61F 2230/0013; A61F 2230/0015; A61F 2230/0041; A61F 2230/0045; A61F 2230/0004
USPC ................. 606/151, 153, 154, 155, 156, 200; 623/1.13, 1.15, 1.23
See application file for complete search history.

(56) References Cited

U.S. PATENT DOCUMENTS

| | | | |
|---|---|---|---|
| 4,249,946 A | | 2/1981 | Danielson |
| 6,132,457 A | * | 10/2000 | Chobotov .................. 623/1.13 |
| 6,139,564 A | * | 10/2000 | Teoh ............................ 606/213 |
| 6,309,367 B1 | * | 10/2001 | Boock .............................. 602/1 |
| 6,361,545 B1 | | 3/2002 | Macoviak et al. |
| 6,371,935 B1 | * | 4/2002 | Macoviak et al. .............. 604/43 |
| 6,395,014 B1 | | 5/2002 | Macoviak et al. |

(Continued)

FOREIGN PATENT DOCUMENTS

| | | |
|---|---|---|
| EP | 2287124 | 2/2011 |
| JP | 11029344 | 2/1999 |

(Continued)

*Primary Examiner* — Jonathan W Miles
(74) *Attorney, Agent, or Firm* — Seager, Tufte & Wickhem LLC

(57) ABSTRACT

The disclosure pertains to porous embolic debris diverters comprising a porous diverter element, a support structure therefor, and a non-hollow flexible elongated retrieval element fixedly attached thereto. The disclosure further pertains to delivery systems for the embolic debris diverters comprising a pusher and an elongated sheath as well as methods of use for the porous embolic debris diverters and the delivery systems therefor. The porous embolic debris diverters are adapted to remain within the body for extended periods of time.

16 Claims, 9 Drawing Sheets

(56) References Cited

U.S. PATENT DOCUMENTS

| | | |
|---|---|---|
| 6,669,680 B1 | 12/2003 | Macoviak et al. |
| 6,695,864 B2 | 2/2004 | Macoviak et al. |
| 6,997,939 B2 | 2/2006 | Linder et al. |
| 7,083,633 B2 | 8/2006 | Morrill et al. |
| 7,137,991 B2 | 11/2006 | Fedie |
| 7,572,288 B2* | 8/2009 | Cox ............... 623/1.17 |
| 7,585,309 B2 | 9/2009 | Larson |
| 7,604,650 B2 | 10/2009 | Bergheim |
| 7,875,051 B2 | 1/2011 | Beulke et al. |
| 7,976,560 B2* | 7/2011 | Denison et al. ............ 606/200 |
| 8,075,585 B2* | 12/2011 | Lee et al. ............ 606/200 |
| 8,114,114 B2 | 2/2012 | Belson |
| 8,206,412 B2 | 6/2012 | Galdonik et al. |
| 8,252,016 B2 | 8/2012 | Anwar |
| 8,252,040 B2* | 8/2012 | Cox ............... 623/1.15 |
| 8,262,692 B2* | 9/2012 | Rudakov ............ 606/200 |
| 8,287,564 B2 | 10/2012 | Beulke et al. |
| 8,308,754 B2 | 11/2012 | Belson |
| 8,388,650 B2* | 3/2013 | Gerberding et al. ........ 606/213 |
| 8,545,530 B2* | 10/2013 | Eskridge et al. ............ 606/191 |
| 8,551,132 B2* | 10/2013 | Eskridge et al. ............ 606/191 |
| 8,715,312 B2* | 5/2014 | Burke et al. ............ 606/200 |
| 2001/0049550 A1* | 12/2001 | Martin et al. ............ 623/1.13 |
| 2003/0158571 A1 | 8/2003 | Esch et al. |
| 2003/0158574 A1 | 8/2003 | Esch et al. |
| 2004/0172055 A1* | 9/2004 | Huter et al. ............ 606/200 |
| 2004/0260331 A1* | 12/2004 | D'Aquanni et al. ......... 606/200 |
| 2005/0101987 A1* | 5/2005 | Salahieh ............ 606/200 |
| 2005/0209634 A1* | 9/2005 | Brady et al. ............ 606/200 |
| 2005/0267516 A1 | 12/2005 | Soleimani et al. |
| 2006/0253148 A1 | 11/2006 | Leone et al. |
| 2006/0271098 A1* | 11/2006 | Peacock, III ............ 606/200 |
| 2007/0027534 A1 | 2/2007 | Bergheim et al. |
| 2007/0123930 A1* | 5/2007 | Huter et al. ............ 606/200 |
| 2007/0156169 A1* | 7/2007 | Denison et al. ............ 606/200 |
| 2007/0225749 A1* | 9/2007 | Martin et al. ............ 606/200 |
| 2008/0039930 A1* | 2/2008 | Jones et al. ............ 623/1.15 |
| 2008/0065145 A1 | 3/2008 | Carpenter |
| 2008/0140110 A1* | 6/2008 | Spence ............ 606/200 |
| 2008/0262532 A1* | 10/2008 | Martin ............ 606/200 |
| 2009/0082800 A1 | 3/2009 | Janardhan |
| 2009/0182371 A1 | 7/2009 | Clausen et al. |
| 2010/0076482 A1 | 3/2010 | Shu et al. |
| 2010/0168785 A1 | 7/2010 | Parker |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185231 A1 | 7/2010 | Lashinski |
| 2010/0191276 A1 | 7/2010 | Lashinski |
| 2010/0211095 A1 | 8/2010 | Carpenter |
| 2010/0312268 A1 | 12/2010 | Belson |
| 2010/0324589 A1 | 12/2010 | Carpenter et al. |
| 2011/0282379 A1 | 11/2011 | Lee et al. |
| 2011/0295304 A1 | 12/2011 | Jonsson |
| 2012/0109182 A1 | 5/2012 | Belson |
| 2012/0172915 A1 | 7/2012 | Fifer et al. |
| 2012/0172916 A1 | 7/2012 | Fifer et al. |
| 2012/0172917 A1 | 7/2012 | Fifer et al. |
| 2012/0172918 A1 | 7/2012 | Fifer et al. |
| 2012/0172919 A1 | 7/2012 | Fifer et al. |
| 2012/0172920 A1 | 7/2012 | Fifer et al. |
| 2012/0179033 A1 | 7/2012 | Merhi |
| 2012/0289996 A1 | 11/2012 | Lee et al. |

FOREIGN PATENT DOCUMENTS

| | | |
|---|---|---|
| WO | 03030750 A1 | 4/2003 |
| WO | 2010026240 A1 | 3/2010 |
| WO | 2011106426 A1 | 9/2011 |

* cited by examiner

EXTENDED PROTECTION EMBOLIC FILTER

BACKGROUND

Preventing emboli and other debris from entering the carotid arteries (i.e., the brachiocephalic artery, or right common carotid artery, and the left common carotid artery) by way of the aorta reduces the incidence of ischemic stroke. Emboli and other debris in the aorta may come from several sources. These sources include: 1) aortic atheroma which detaches from the wall of the aorta due to various reasons including incising, clamping, and/or clamp release of the aorta during surgery; 2) debris released during surgery on the heart such as the installation of a replacement heart valve; 3) thrombus which forms in the right atrium resulting from atrial fibrillation; 4) thrombus which forms on ventricular assist devices; 5) venous thrombus which passes into the left ventricle through a patent foramen ovale or other arteriovenous shunt; and 6) other less common sources.

A variety of intravascular filtering means are known in the art and may consist of a flexible metallic grid, a flexible synthetic or plastic grid, a weave of synthetic filaments, or a nondegradable or possibly biodegradable textile cloth, often supported by a basket or funnel shaped frame which may be deployed within the lumen of a vessel to be protected.

There are fewer intravascular devices designed for arterial and especially aortic filtration, much less diversion. An embolic debris diverter that functions in arteries must address additional concerns because of the hemodynamic differences between arteries and veins. Arteries are much more flexible and elastic than veins and, in the arteries, blood flow is pulsatile with large pressure variations between systolic and diastolic flow. These pressure variations cause the artery walls to expand and contract. Thus, filters and diverters must be able to expand and contract along with the lumen of the aorta to which they may be anchored. In addition, intravascular devices for aortic filtration and/or diversion of emboli typically occlude a significant portion of the lumen of the aorta rendering them unsatisfactory for use in combination with other intravascular interventional procedures.

Although the majority of debris is expected to be generated during a treatment or diagnostic procedure, it is known that the potential for ischemic stroke persists for a period of time after surgery. The problem of preventing emboli from reaching the cerebral vasculature following surgical intervention has thus far not been adequately addressed. Therefore, a need exists for new devices and methods to prevent embolic material from entering the carotid/cerebral arteries, while maintaining peripheral blood flow from the heart to the descending aorta. Such devices should be capable of remaining within the body for an extended period of time before being removed.

SUMMARY

This disclosure pertains to embolic protection devices which are adapted to be deployed with in a vessel, such as an aorta, to remain deployed within the aorta for an extended post-operative time, and to be retrieved from the vessel by retracting a non-hollow flexible elongated retrieval element attached to the embolic protection device relative to a retrieval device.

In some embodiments, the embolic protection device comprises a porous diverter element having a distal opening; a support structure connected to the distal opening of the porous diverter element; and a non-hollow flexible elongated retrieval element having a distal end and a proximal end, wherein the distal end is fixedly affixed to at least one of the porous diverter element and the support structure and the proximal end is adapted to remain outside of the body, further wherein the embolic protection device has a first compressed state and a second expanded deployed state.

In other embodiments, the disclosure relates to an embolic protection device delivery system comprising an embolic protection device and a pusher having a distal end and a proximal end, wherein the distal end of the pusher is adapted to engage a proximal end of at least one of the porous diverter element and the support structure when the embolic protection device in the first compressed state.

In yet other embodiments, the disclosure relates to methods of preventing debris from entering a carotid artery for an extended period of time comprising disposing an embolic protection device, comprising a porous diverter, a support structure and a non-hollow flexible elongated retrieval element, in a first compressed state and a pusher having a distal end and a proximal end within a lumen of an elongated sheath, wherein the distal end of the pusher is adapted to engage a proximal end of at least one of the porous diverter element and the support structure when the embolic protection device in a first compressed state, wherein the non-hollow flexible elongated retrieval element of the embolic protection device extends from proximate the distal end of the pusher through the lumen of the sheath and exits the proximal end of the sheath; advancing the embolic protection device in a first compressed state, the pusher, and the elongated sheath through a vessel to a position proximate a deployment site; advancing the pusher distally within the lumen of the elongated sheath, thereby ejecting the embolic protection device in a first compressed state and allowing the embolic protection device to assume a second deployed state; withdrawing the sheath from the vessel; withdrawing the pusher from the vessel; waiting a specified period of time; inserting a retrieval device for the embolic protection device along the non-hollow flexible elongated retrieval element of the embolic protection device to a point proximate the proximal end of the embolic protection device; withdrawing the non-hollow flexible elongated retrieval element of the embolic protection device relative to the retrieval device until the embolic protection device is at least partially contained within the retrieval device; and withdrawing the embolic protection device, the non-hollow flexible elongated retrieval element, and the retrieval device from the vessel.

As is conventional with devices exposed to blood during use, components of the devices disclosed herein may include antithrombogenic coatings or may be designed to elute antithrombogenic drugs.

DETAILED DESCRIPTION

Figure 1:
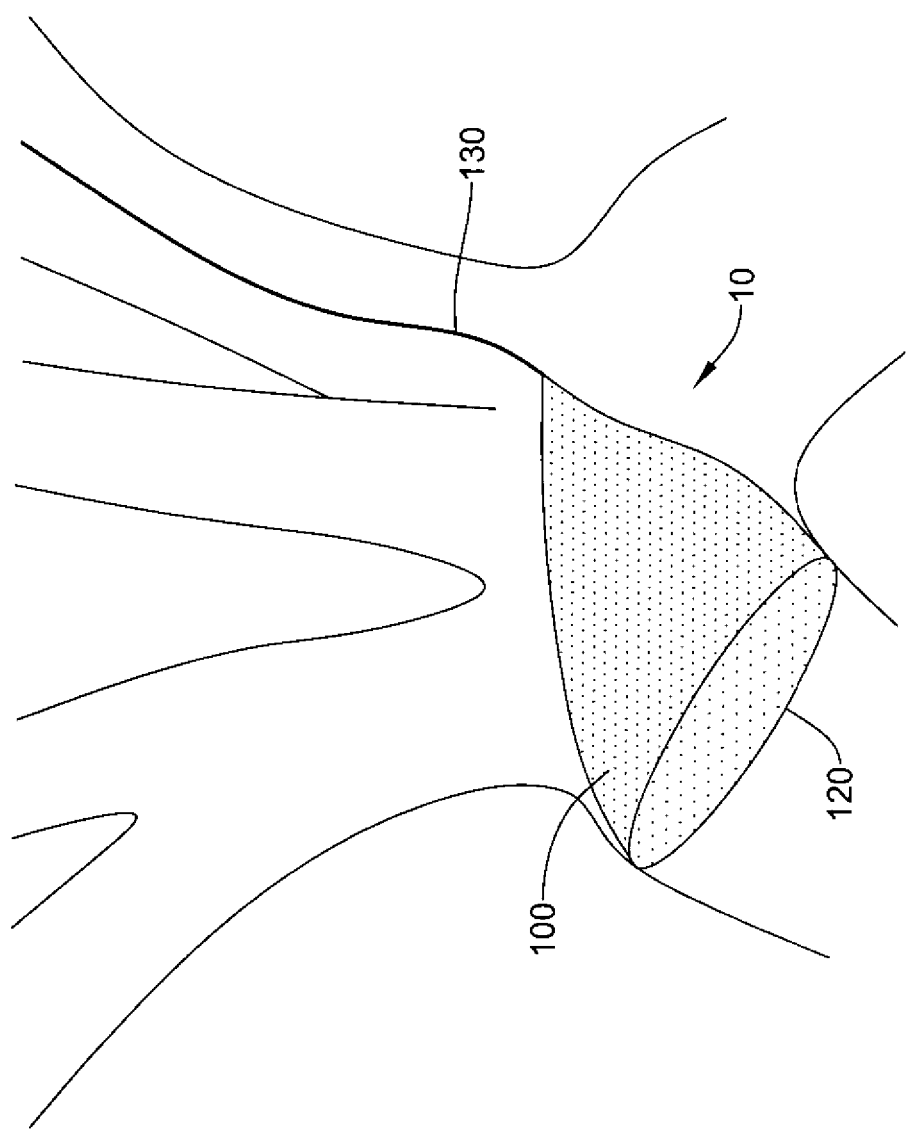
FIG. 1 illustrates an embodiment of the porous embolic debris deflector of the disclosure.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary.

As used herein, the term "suture" should be broadly interpreted to include various flexible elongated biocompatible elements generally resembling a string or thread in shape and size. A suture may comprise a monofilament or multifilament structure of natural materials, synthetic materials, and combinations thereof. Further, a suture may be either bioabsorbable or non-bioabsorbable. Typically sutures suitable for use in the articles of the disclosure are substantially non-bioabsorbable on the time scale of their intended use. Some porous diverters and/or their associated sutures of the disclosure may include one or more of a radiopaque or MRI visible marker. Such markers are understood to be well known in the art and need not be explicitly described and illustrated.

As used herein with respect to a embolic protection device as a whole, a distal and/or proximal "opening" is to be broadly interpreted as encompassing embodiments in which the respective distal or proximal end of the porous diverter and/or an associated support structure may form a complete closed loop and/or may only contact a portion of the lumen of a vessel in which the embolic protection device is deployed. In the latter configurations, the lumen of the vessel at the appropriate portion of the porous diverter may be said to define, in part, the "opening". Accordingly the "opening" associated with an embolic protection device may, in some embodiments, comprise a limited arc comprising the porous diverter and/or support structure lying along a vessel wall and the adjacent vessel wall. In some embodiments, the opening thus defined may lie generally transverse to the axis of the vessel, while in other embodiments, the opening may lie in a plane approximately parallel to the axis of the vessel, or at intermediate angles to the axis of the vessel. In certain embodiments, an opening associated with an embolic protection device may be defined, in part, by a support structure. In certain other embodiments, the opening may be defined, in part, by the porous diverter element. In general, it will be appreciated that "openings" associated with an embolic protection device correspond to a cross-section of the largely unobstructed lumen of the vessel in which the embolic protection device is deployed.

FIG. 1 illustrates an embolic protection device 10 of the disclosure deployed within an aorta such that emboli carried by the blood flow are prevented from entering the brachiocephalic artery, or right common carotid artery, and the left common carotid. As depicted, the embolic protection device 10 also provides a degree of protection to the left subclavian artery through which the device has been advanced prior to deployment. The embolic protection device 10 comprises a porous diverter element 100 supported at its distal end by a support structure in the form of loop 120 and a non-hollow flexible elongated retrieval element 130 having a distal end and a proximal end, wherein the distal end is fixedly affixed to at least one of the porous diverter element 100 and the support structure 120. The porous diverter 100 comprises a sheet or membrane-like material similar to those commonly employed to construct embolic filters. In some embodiments, the porous diverter element 100 may be a polymeric or metal sheet with holes therethrough which are sized to allow blood to pass through largely unimpeded, but small enough to prevent harmful emboli from entering the vessels which are at least partially covered by the porous diverter element 100. For example, such holes may be laser cut holes. The holes may take any of the forms commonly employed for embolic filter membranes. The holes may, for example, be round, oval, square, rectangular, diamond-shaped, linked diamond-shapes, lobed openings, and the like.

In other embodiments, the porous diverter element 100 may comprise a woven or nonwoven sheet such as a braid or mesh having interstices of an appropriate size. In yet other embodiments to be discussed herein the porous diverter element 100 may comprise somewhat larger interstices which include finger-like protrusions extending into the openings to reduce the obstruction presented to blood flow while limiting the size of particles which may pass through the openings.

The support structure 120 of FIG. 1 has the form of a complete loop which spans the vessel. As illustrated, loop support structure 120 is deployed across an aorta at an angle to the longitudinal axis of the vessel which allows the loop support structure 120 to be deployed in aortae of various size and to better accommodate the changes in the diameter of the aorta as the artery walls expand and contract in response to large pressure variations between systolic and diastolic flow.

Support structure 120 typically is elastically resilient and may be formed from, for example, wire or ribbon. The wire or ribbon may be, for example, Nitinol, stainless steel, polymer or other suitable material. In some embodiments, support structure 120 may be integrally formed with the porous diverter element 100. Although depicted in FIG. 1 as a perimeter loop, it will be appreciated that any of the support structures of this disclosure may also include ribs (not shown) which further support the porous diverter element. Such ribs may be transverse, longitudinal or combinations thereof. In some embodiments, the ribs may be patterned in leaf vein-like or fishbone-like branched structures. Not all ribs need have the same length and/or cross-section.

The porous diverter element 100 is fixedly attached to the support structure 120 around the perimeter of the loop. The attachment may be continuous or intermittent. In some embodiments the attachment may be provided by wrapping the distal edge of the porous diverter element 100 around the support structure 120 and bonding the distal edge of the porous diverter element 100 to the diverter element thereby forming a tube which contains the support structure 120. For the purposes of this disclosure, a containing tube so formed will be considered to be fixedly attached to the support structure 120.

Proximal of the support structure 120, porous diverter element 100 opens in the form of a cylinder which has been sliced at an angle to the longitudinal axis such that the circumferential width of the porous diverter element 100 varies from the full circumference of the support structure 120 at the distal opening to a somewhat narrower strip at the proximal end at which it is attached to the distal end of the non-hollow flexible elongated retrieval element 130. It will be appreciated that the circumferential width of the porous diverter element 100 may vary in any desired manner depending on the degree to which it is desirable to cover the ostia of the vessels to be protected. For example, the circumferential width of the porous diverter element 100 in FIG. 1 remains wide enough to fully cover the ostium of the left carotid artery before tapering to provide only partial coverage of the left subclavian artery at its proximal end.

The non-hollow flexible elongated retrieval element 130 is fixedly attached to the proximal end of the porous diverter element 100 and typically has the form of a biocompatible string or suture. As noted herein, the non-hollow flexible elongated retrieval element 130 may comprise a monofilament or multifilament structure of natural materials, synthetic materials, and combinations thereof. Further, the non-hollow flexible elongated retrieval element 130 may be either bioabsorbable or non-bioabsorbable. Typically non-hollow flexible elongated retrieval elements 130 suitable for use in the articles of the disclosure are substantially non-bioabsorbable on the time scale of their intended use. In each of the embodiments disclosed herein, the materials used for constructing the components or coatings applied thereto may be selected to be antithrombogenic or to elute an antithrombogenic drug. In certain embodiments, a metal wire or ribbon may serve as the non-hollow flexible elongated retrieval element 130.

In general, a non-hollow flexible elongated retrieval element associated with an embolic protection device of the disclosure is deployed within the vessel through which the embolic protection device has been introduced to the deployment site, typically the left subclavian artery. In some embodiments, a non-hollow flexible elongated retrieval element may extend from the body at the insertion site through a transcutaneous port adapted to seal the non-hollow flexible elongated retrieval element for the duration of the temporary implantation of the embolic protection devices of the disclosure. In various embodiments, the embolic protection devices of the disclosure may be adapted to remain deployed in a vessel for 1, 2, 4, 8, 24, 48, 72, 168 or more hours following completion of a diagnostic or interventional procedure performed upstream of the embolic protection device. Following a suitable protection period, a retrieval device may be inserted into the vessel over the non-hollow flexible elongated retrieval element whereupon the porous deflector element and support structure may be withdrawn into the retrieval element for removal. The non-hollow flexible elongated retrieval elements of the disclosure allow the disclosed porous deflector elements and support structures to be easily retrieved, but do not require that the non-hollow flexible elongated retrieval elements remain taut throughout the indwelling period, thereby allowing the patient a greater range of motion.

Figure 2:
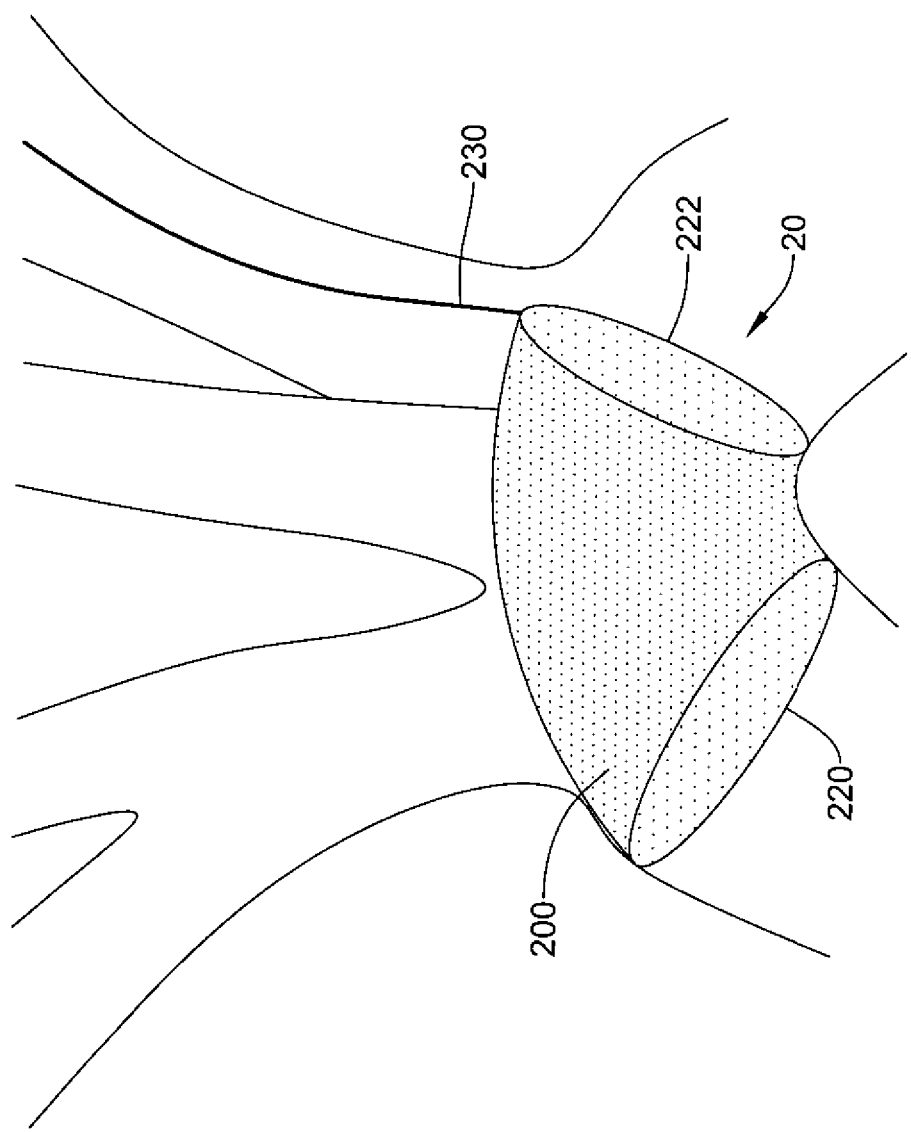
FIG. 2 illustrates a second embodiment of the porous embolic debris deflector of the disclosure.

In the embodiment of FIG. 2, the support structure 220, 222 of the embolic protection device 20 takes the form of two loops and the porous diverter element 200 takes a somewhat more tubular form therebetween. As in the embodiment of FIG. 1, the support structures 220, 222 are typically not positioned strictly transverse to the axis of the vessel in which the device is deployed. Indeed in some embodiments, support structure loop 222 is significantly angled relative to the axis of the vessel.

Other details of the embolic protection device 20, such as structure and materials, are similar to those detailed with regard to the embodiment of FIG. 1. In some embodiments of FIGS. 1 and 2, portions of the porous diverter elements 100, 200 may be sufficiently elastomeric, or may be intentionally deformed, to produce a protruding region 202 (FIG. 3) which helps to position the porous diverter element and to prevent undesirable translation of the embolic protection device once the device is positioned. As illustrated, the protruding region 202 may partially enter the ostium of at least one of the vessels to be protected. It will be appreciated that more than one protruding region, resembling region 202, may be present and that such protruding regions may engage more than one ostium if desired.

Figure 3:
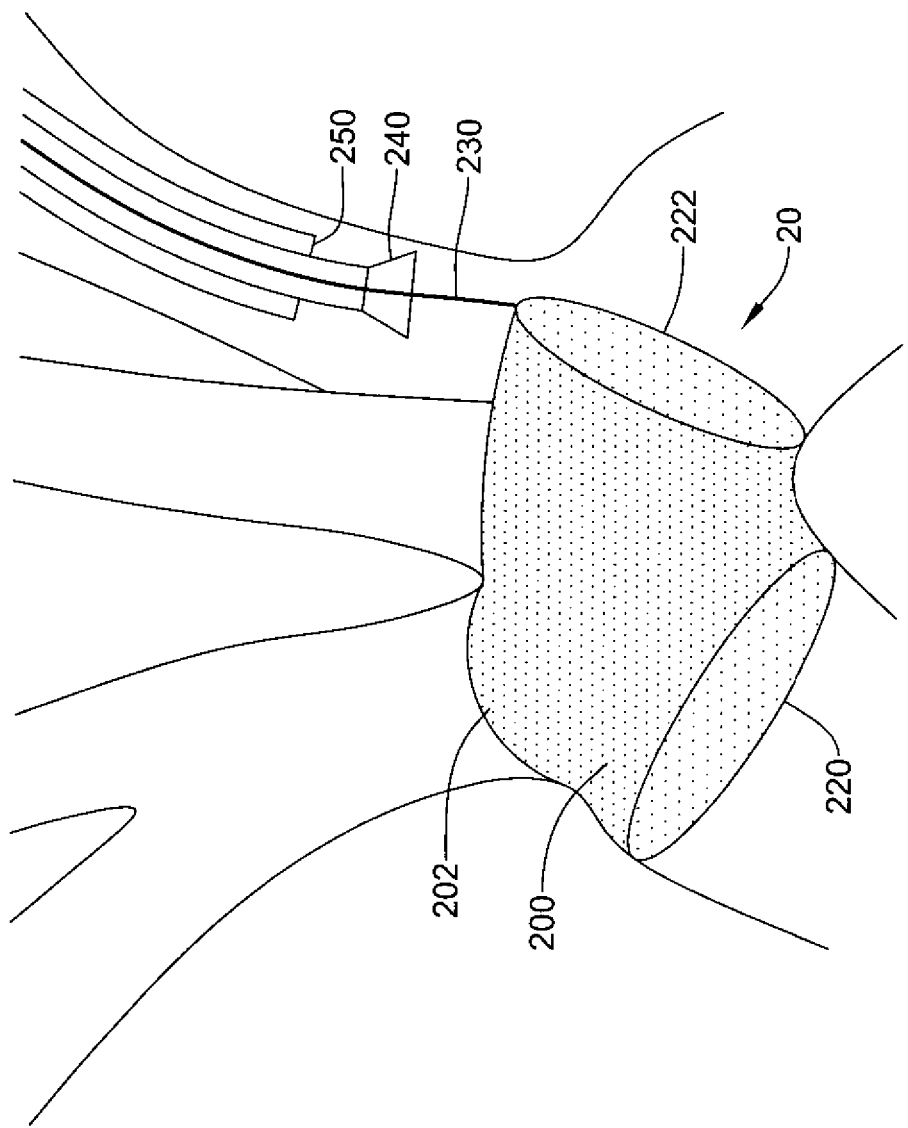
FIG. 3 illustrates a variation of the second embodiment of the porous embolic debris deflector of the disclosure.

FIG. 3 also illustrates, somewhat schematically, other elements of an embolic protection device delivery system which may be employed with any of the embolic protection devices of this disclosure. For non-limiting purposes of illustration, an embolic protection device delivery system for the embolic protection device 20 of FIG. 3 will be described. Initially, the porous diverter 200 and its associated support structures 220, 222 are present in a first compressed state within an elongated sheath 250, typically near the distal end thereof. A pusher 240 is disposed about the non-hollow flexible elongated retrieval element 230 of the embolic protection device 20 and distal thereof within the elongated sheath 250. In some embodiments, the pusher 240 will include a lumen connecting the distal end with the proximal end thereof and the non-hollow flexible elongated retrieval element 230 of the embolic protection device 20 will extend therethrough to a position outside of the body. In other embodiments, the pusher 240 may have a short distal lumen (not shown) for the non-hollow flexible elongated retrieval element 230 of the embolic protection device 20 which may function as a rapid exchange lumen for the non-hollow flexible elongated retrieval element 230. In such embodiments, the intermediate and proximal portions of the pusher may be replaced by a solid shaft or wire if desired.

In many embodiments, the pusher 240 may include a somewhat enlarged distal end to better engage the proximal end of the first compressed state of porous diverter 200 and its associated support structures 220, 222. When the distal end of the elongated sheath 250 is positioned proximate the desired deployment location, pusher 240 may be advanced within the elongated sheath 250 to eject the porous diverter 200 and its associated support structures 220, 222, which then assume a second deployed state within the vessel. Thus pusher 240 provides a function which is not provided by the non-hollow flexible elongated retrieval element 230 which lacks pushability. Pusher 240 may be made from any biocompatible material(s) and/or construction which is sufficiently stiff to provide pushability and sufficiently flexible to navigate the vessel through which the embolic protection device 20 is delivered.

Elongated sheath 250 includes a lumen sized and adapted to receive at least a portion of the embolic protection device 20 in a first collapsed state and at least the distal portion of pusher 240. As with pusher 240, the lumen of elongated sheath 250 need not extend the entire length of the delivery system, but may comprise a tubular distal portion and a solid intermediate and/or proximal shaft portion formed from pushable biocompatible materials such as metals and/or polymers. Although they are not expressly illustrated in combination to avoid unnecessary repetition, it will be appreciated that any of these variations of pusher and/or elongated sheath may be used in combination to deliver any of the embolic protection devices 10, 20, 30, 50, 60, and/or 70 described herein, or their variants.

Figure 4:
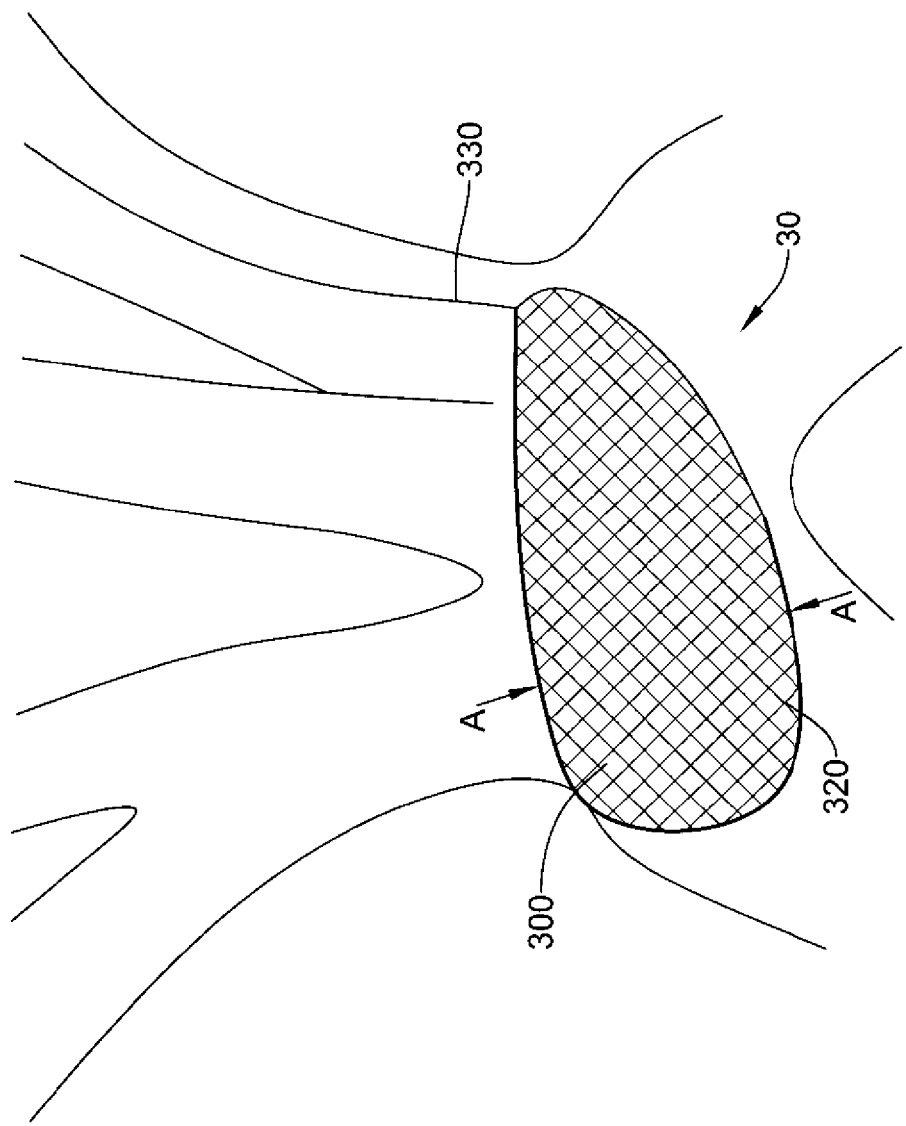
FIG. 4 illustrates a third embodiment of the porous embolic debris deflector of the disclosure.
Figure 4A:
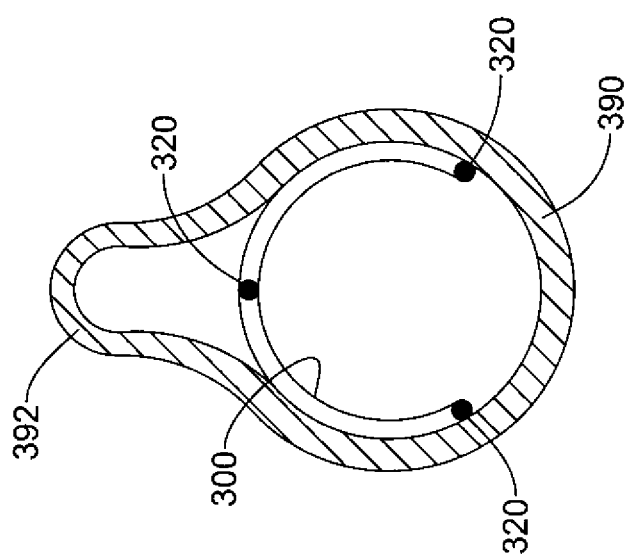
FIG. 4A illustrates a cross-sectional view of the embodiment of FIG. 4 deployed within a vessel.

FIG. 4 illustrates one such variant embolic protection device 30 in which a saddle-like porous diverter element 300 and its support structure 320 do not form a complete circumferential loop when deployed within a vessel. Instead, the support structure 320 is adapted to subtend between 180 and 359 degrees of the circumference of the vessel at least one position along the support structure's length. See, for example, FIG. 4A in which a transverse cross-section of the aorta 390 and a portion of the brachiocephalic artery 392 illustrate the incomplete loop spanned by support structure 320 and porous diverter element 300. In other variations, the support structure may subtend more than 359 degrees of the circumference of the vessel to overlap, particularly in smaller or partially occluded vessels. As in the earlier variants, the embolic protection device includes a non-hollow flexible elongated retrieval element 330 which may be used in conjunction with any of the pushers and elongated sheaths described herein to form an embolic protection device delivery system. As in the embodiment of FIG. 3, an embolic protection device 30 may include one or more protruding regions (not shown), which may partially enter the ostium of at least one of the vessels to be protected. Although the embodiment of FIG. 4 has been illustrated as employing a porous diverter 300 which is coextensive with the support structure 320, it will be appreciated that one or more portions (not shown) of the support structure may extend further around the circumference of the vessel in which the device is deployed than the porous diverter portion 300 does. The materials and construction employed for the embolic protection device 30 of FIG. 40 may be substantially the same as those described for other variants herein.

Figure 5:
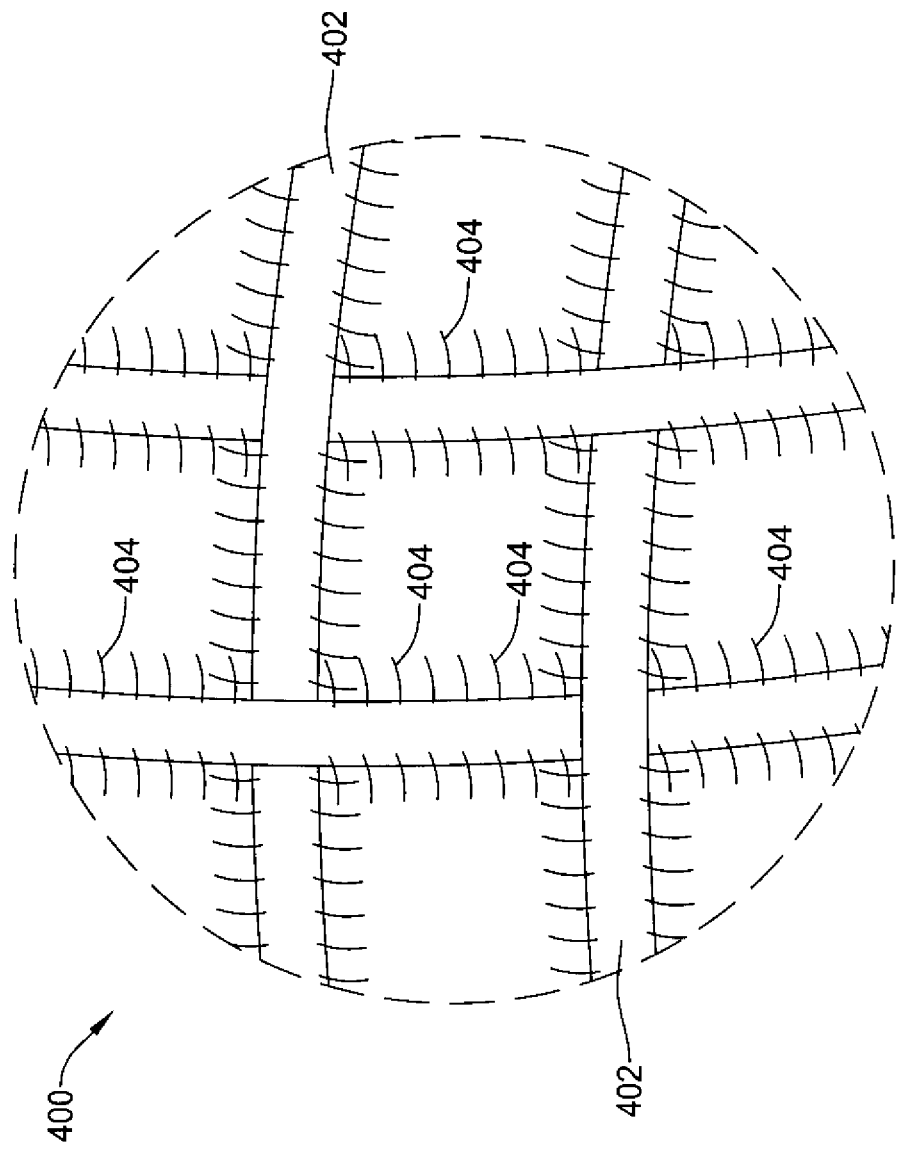
FIG. 5 illustrates a portion of a porous embolic debris deflector of the disclosure.

As discussed earlier herein, the nonporous diverter 400, shown in a detail in FIG. 5, may include a relatively open woven mesh or braid which may pivot or flex at the crossing points of the strands 402 thereof to allow the nonporous diverter 400 to collapse into a first compressed state more readily. In addition to the primary strands 402, the nonporous diverter 400 may include fingers or cilia 404 which protrude into the interstices defined by the primary strands 402. The cilia 404 may be integral with the primary strands 402 and formed simultaneously therewith or may be separate structures formed from the same or different material and added at a later time. In this way, a nonporous diverter 400, which might otherwise be stiffer than desired if formed only with small interstices between primary strands 402, may remain more flexible as the cilia 404 block larger particles from passing through the porous diverter while allowing the structure of the braid or mesh to remain relatively open.

Figure 6:
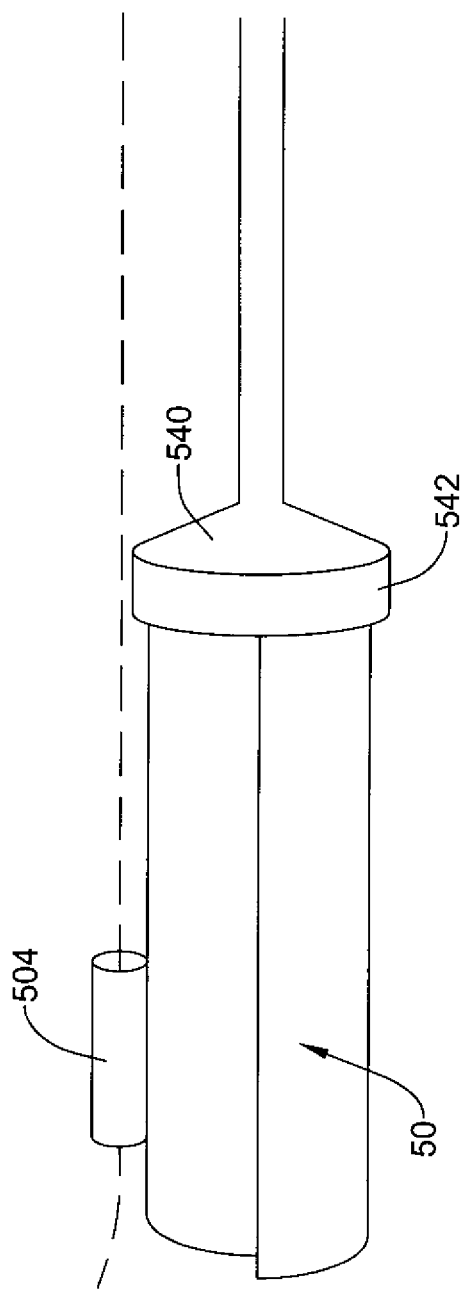
FIG. 6 illustrates variations of portions of an embodiment of the disclosure.

FIG. 6 illustrates additional optional features which may be incorporated into any embolic protection device delivery system of the disclosure. In the figure, details of the porous diverter and support structures associated with the embolic protection device 50 have been omitted for clarity. The embolic protection device 50 is illustrated in a coiled first compressed state. Embolic protection device 50 may include a tubular element 504 having a guidewire lumen therethrough for receiving a guidewire shown in phantom in the figure. The tubular element 504 may serve to guide the embolic protection device 50 along a guidewire to the desired deployment location and further may serve to orient the embolic protection device 50 within the vessel. For example, if the embolic protection device 50 is to be introduced through the left subclavian artery to minimize the likelihood that any debris generated during the insertion or removal of the embolic protection device 50 will reach the right or left common carotid artery, a guidewire advanced through the left subclavian artery may be directed partially into the ostium of the brachiocephalic or right subclavian artery to orient the advancing embolic protection device 50 as the time of deployment and then may be removed with or separately from the elongated sheath (not shown) or pusher 540.

As further illustrated in FIG. 6, pusher 540 includes an optional collar 542 which partially surrounds the proximal end of the porous diverter and/or support structure (not shown in detail) to provide improved support and guidance. Although the collar 542 is shown as a solid body, it will be appreciated that in some embodiments a plurality of finger-like extensions may serve a similar purpose. The modified pusher 540 may replace any pusher of the disclosure.

Figure 7:
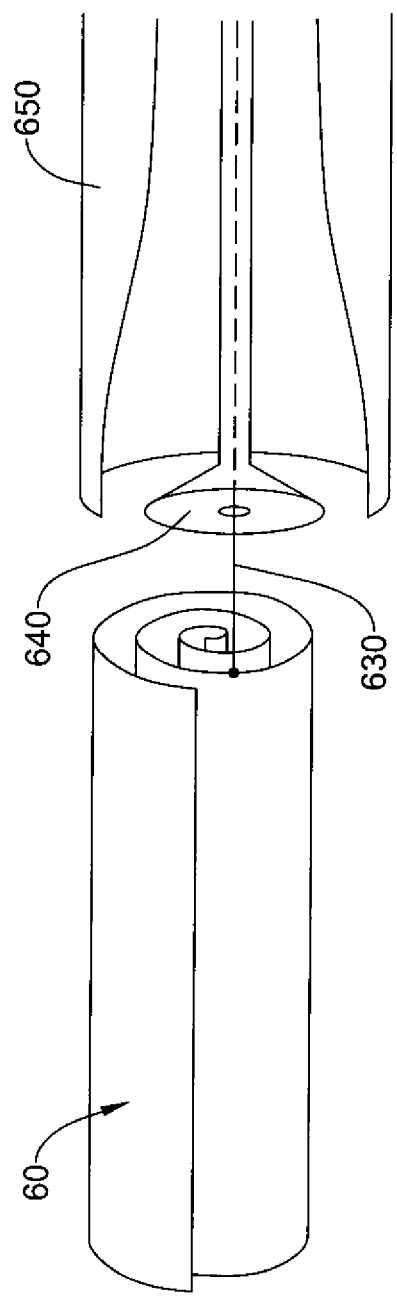
FIG. 7 illustrates a portion of an embolic protection device delivery system of the disclosure.

FIG. 7 illustrates somewhat schematically a coiled porous diverter/support structure of an embolic protection device of the disclosure as it might be disposed during delivery. Elongated sheath 650 is shown in partial cutaway to reveal a pusher 640 having an enlarged distal end and a hollow shaft adapted to slidably contain a non-hollow flexible elongated retrieval element 630. During retrieval, a similar elongated sheath may be advanced over non-hollow flexible elongated retrieval element 630 to engulf the porous diverter/support structure of the embolic protection device. Although it is not explicitly illustrated, the distal end of the elongated sheath used for retrieval may include one or more features adapted to direct the porous diverter/support structure of the embolic protection device to adopt a configuration which is better suited for retrieval, for example, the coiled configuration of FIG. 7.

Figure 8:
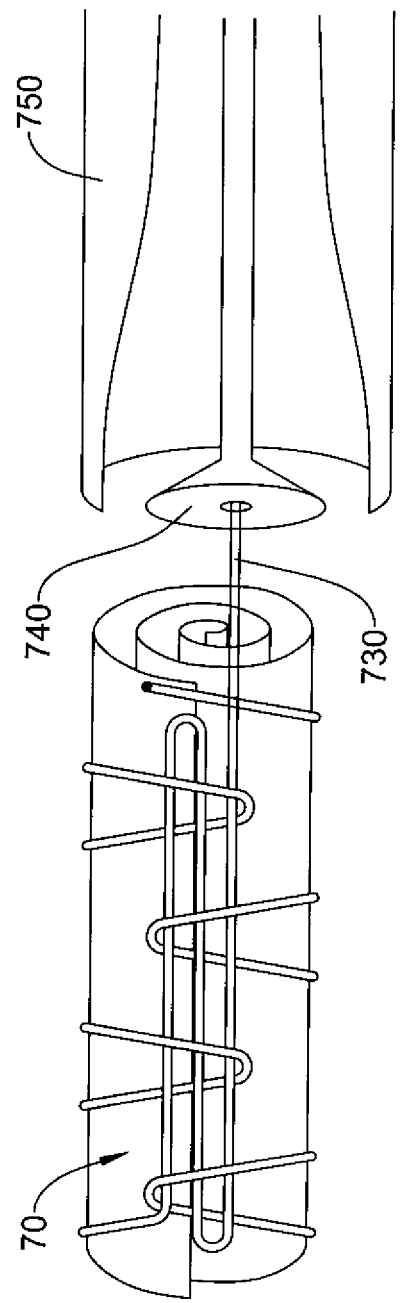
FIG. 8 illustrates an optional element of an embolic protection device delivery system of the disclosure.

In some embodiments, it may be useful to include a releasable covering or restraint which tends to maintain the first compressed configuration of the porous diverter/support structure of the embolic protection device until the porous diverter/support structure is fully ejected from the elongated sheath of an embolic protection device delivery system and properly positioned. In some such embodiments, as illustrated in FIG. 8, a restraint may be formed by wrapping a portion of a non-hollow flexible elongated retrieval element 730 around the porous diverter/support structure of an embolic protection device 70 such that when tension is applied to the non-hollow flexible elongated retrieval element 730 and the proximal force is resisted by the distal end of pusher 740, the non-hollow flexible elongated retrieval element 730 is released from the porous diverter/support structure of the embolic protection device 70. In certain embodiments, the non-hollow flexible elongated retrieval element 730 may be self-holding in the absence of applied tension, while in certain other embodiments, the embolic protection device 70 may include various latches or temporary adhesives to prevent premature release of the non-hollow flexible elongated retrieval element 730. In yet other embodiments, a separate restraint and release actuator (not shown) may be employed. As with other variations, a restrain system of FIG. 8 may be incorporated in any of the embolic protection device delivery systems described herein. For example, in certain embodiments, a restraint system of FIG. 8 may be combined with a pusher collar of FIG. 6 to result in a deployment system which may not require an elongated sheath for delivery, particularly if a tubular element of FIG. 6 is employed in conjunction with a guidewire to direct the apparatus to the desired deployment site.

In use, the embolic protection device delivery systems described herein may be employed as follows. An embolic protection device delivery system comprising one of the embolic protection devices described, an elongated sheath, and a pusher may be advanced through the vasculature to a suitable deployment site. The pusher of the embolic protection device delivery system may be used to advance the porous diverter and/or support structure beyond the distal end of the elongated sheath whereupon the porous diverter and/or support structure are allowed to deploy thereby positioning the porous diverter to allow blood to enter the adjacent diverging vessels while diverting debris away from adjacent diverging vessels, such as the right and left common carotid arteries, while the diverter is allowed to remain in the body during a post-operative period which may be 1, 2, 4, 8, 24, 48, 72, 168 or more hours. Once the porous diverter and/or support structure have been deployed, the pusher and/or the elongated sheath may be removed from the vessel while the embolic protection device remains within the body.

When the protective function is no longer desired, a suitable retrieval device of the art, which may resemble the elongated sheath of the embolic protection device delivery system, may be advanced over the non-hollow flexible elongated retrieval element whereupon the porous deflector element and support structure may be withdrawn at least partially into the retrieval element for removal by applying tension to the non-hollow flexible elongated retrieval element when the retrieval device is positioned proximate the proximal end of the porous diverter and/or support structure. The retrieval device and the embolic protection device may then be removed from the body.

Although the illustrative examples described above relate to an embolic protection device to be deployed in an aorta to prevent debris from entering the carotid arteries, it is also contemplated that related devices are useful in other portions of the body in which a sensitive tissue may be protected from embolic debris, which may be circulating within the vasculature for a period of time following a diagnostic and/or interventional procedure. In such an embodiment, details of the shape and preferred deployment path may be altered as desired.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. An embolic protection device comprising:
   a porous diverter element having a distal opening;
   a support structure connected to the distal opening of the porous diverter element; and
   a non-hollow flexible elongated retrieval element having a distal end and a proximal end, wherein the distal end is fixedly affixed to at least one of the porous diverter element and the support structure and the proximal end is adapted to remain outside of the body,
   further wherein the embolic protection device has a first compressed state and a second expanded deployed state wherein the distal opening of the porous diverter element does not form a closed loop, and wherein the support structure includes a partial loop supporting the distal opening of the porous diverter element.

2. The embolic protection device of claim 1, wherein the non-hollow flexible elongated retrieval element fixedly affixed to at least one of the porous diverter element and the support structure is a suture.

3. The embolic protection device of claim 1, further wherein the porous diverter element has a proximal opening.

4. The embolic protection device of claim 1, wherein the partial loop of the support structure supporting the distal opening of the porous diverter element is sized and adapted to subtend between 180 degrees and 359 degrees of the circumference of a vessel in which it is deployed.

5. The embolic protection device of claim 1, wherein the embolic protection device has a first delivery configuration in which a portion of the non-hollow flexible elongated retrieval element is wrapped around the porous diverter element thereby maintaining the embolic protection device in the first compressed state and a second deployed configuration in which the non-hollow flexible elongated retrieval element has been unwrapped from around the porous diverter element allowing the embolic protection device to assume the second expanded deployed state within the body.

6. The embolic protection device of claim 1, wherein at least one of the porous diverter element and the support structure further comprises a tubular portion having a lumen adapted to slidably receive a guidewire.

7. An embolic protection device delivery system comprising:
   the embolic protection device of claim 1 and
   a pusher having a distal end and a proximal end,
   wherein the distal end of the pusher is adapted to engage a proximal end of at least one of the porous diverter element and the support structure when the embolic protection device in the first compressed state.

8. The embolic protection device delivery system of claim 7, further wherein the pusher distal end includes an extension which at least partially surrounds the proximal end of at least one of the porous diverter element and the support structure when the embolic protection device in the first compressed state.

9. The embolic protection device delivery system of claim 7, further comprising an elongated sheath having a lumen with a distal end and a proximal end,
   wherein the distal end of said lumen is adapted to slidably receive the pusher and the proximal end of at least one of the porous diverter element and the support structure when the embolic protection device in the first compressed state.

10. The embolic protection device delivery system of claim 9, wherein the proximal end of the lumen of the elongated sheath is adapted to slidably receive the pusher and the non-hollow flexible elongated retrieval element of the embolic protection device.

11. The embolic protection device delivery system of claim 9, wherein the sheath is adapted to be removed from the non-hollow flexible elongated retrieval element of the embolic protection device when the embolic protection device is in the second expanded deployed state.

12. The embolic protection device delivery system of claim 7, wherein the pusher further includes a lumen adapted to slidably receive the non-hollow flexible elongated retrieval element of the embolic protection device.

13. The embolic protection device delivery system of claim 12, wherein the pusher lumen adapted to slidably receive the non-hollow flexible elongated retrieval element of the embolic protection device extends from the distal end to the proximal end of the pusher.

14. The embolic protection device delivery system of claim 12, wherein the pusher is adapted to be removed from the non-hollow flexible elongated retrieval element of the embolic protection device when the embolic protection device is in the second expanded deployed state.

15. A method of preventing debris from entering a carotid artery for an extended period of time comprising:
- disposing an embolic protection device of claim 1 in a first compressed state and a pusher having a distal end and a proximal end within a lumen of an elongated sheath,
- wherein the distal end of the pusher is adapted to engage a proximal end of at least one of the porous diverter element and the support structure when the embolic protection device in a first compressed state,
- wherein the non-hollow flexible elongated retrieval element of the embolic protection device extends from proximate the distal end of the pusher through the lumen of the sheath and exits the proximal end of the sheath;
- advancing the embolic protection device in a first compressed state, the pusher, and the elongated sheath through a vessel to a position proximate a deployment site;
- advancing the pusher distally within the lumen of the elongated sheath, thereby ejecting the embolic protection device in a first compressed state thereby allowing the embolic protection device to assume a second deployed state;
- withdrawing the sheath from the vessel;
- withdrawing the pusher from the vessel;
- waiting a specified period of time;
- inserting a retrieval device for the embolic protection device along the non-hollow flexible elongated retrieval element of the embolic protection device to a point proximate the proximal end of the embolic protection device;
- withdrawing the non-hollow flexible elongated retrieval element of the embolic protection device relative to the retrieval device until the embolic protection device is at least partially contained within the retrieval device; and
- withdrawing the embolic protection device, the non-hollow flexible elongated retrieval element, and the retrieval device from the vessel.

16. The method of claim 15, wherein the step of advancing the embolic protection device of claim 1 in a first compressed state, the pusher, and the elongated sheath through a vessel comprises advancing the embolic protection device in a first compressed state, the pusher, and the elongated sheath through a left subclavian artery to an aorta.

* * * * *